United States Patent [19]
Ogata et al.

[11] Patent Number: 5,789,409
[45] Date of Patent: Aug. 4, 1998

[54] BENZYLPIPERAZINE DERIVATIVE

[75] Inventors: Kazumi Ogata, Osaka; Kazuhiko Ito, Amagasaki; Takahiro Sakaue, Itami; Shinya Ogino, Itami, all of Japan

[73] Assignee: Senju Pharmaceutical Co., Ltd., Osaka, Japan

[21] Appl. No.: 677,115

[22] Filed: Jul. 9, 1996

[30] Foreign Application Priority Data

Jul. 10, 1995 [JP] Japan .................................. 7-173085
Nov. 30, 1995 [JP] Japan .................................. 7-311772

[51] Int. Cl.$^6$ ...................... A61K 31/50; C07D 401/00
[52] U.S. Cl. ...................... 514/252; 514/252; 544/360; 544/392; 544/400
[58] Field of Search .................. 514/252; 544/360, 544/392, 400

[56] References Cited

U.S. PATENT DOCUMENTS

| | | | |
|---|---|---|---|
| 4,234,585 | 11/1980 | Winter et al. | 424/250 |
| 4,725,597 | 2/1988 | Devlin et al. | 514/252 |
| 5,047,404 | 9/1991 | Coates et al. | 514/243 |

FOREIGN PATENT DOCUMENTS

| | | |
|---|---|---|
| 0 058 146 | 8/1982 | European Pat. Off. . |
| 0 122 488 | 10/1984 | European Pat. Off. . |
| 0 127 182 | 12/1984 | European Pat. Off. . |
| 0 624 584 | 11/1994 | European Pat. Off. . |
| 2 827 566 | 1/1980 | Germany . |
| 5-345 765 | 12/1993 | Japan . |

*Primary Examiner*—Johann Richter
*Assistant Examiner*—Joseph Murray
*Attorney, Agent, or Firm*—Wenderoth, Lind & Ponack

[57] ABSTRACT

This invention provides a benzylpiperazine derivative of formula (I) and a pharmacologically acceptable salt thereof

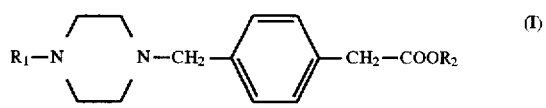

wherein $R_1$ represents a pyridine ring or a group of either formula (IV) or formula (V); $R_2$ represents hydrogen or lower alkyl

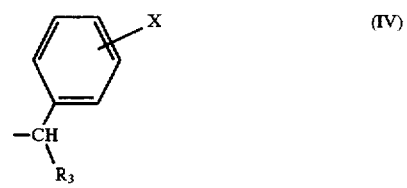

wherein $R_3$ represents hydrogen, lower alkyl, a pyridine ring or a benzene ring which may be substituted by halogen; X represents halogen

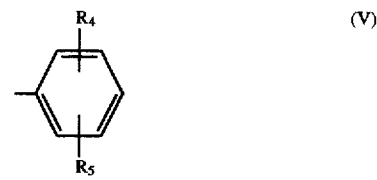

wherein $R_4$ and $R_5$ may be the same or different and each represents hydrogen, lower alkyl, lower alkoxy, halogen or carboxy.

22 Claims, 2 Drawing Sheets

5,789,409

BENZYLPIPERAZINE DERIVATIVE

BACKGROUND OF THE INVENTION

1. Field of the Invention

The present invention relates to a novel and useful benzylpiperazine derivative, a process for producing the derivative, and an antiallergic composition and an antiinflammatory composition both containing said derivative as an active ingredient.

2. Description of the Prior Art

A variety of antiallergic drugs are known and, as a piperazine derivative having antiallergic activity, oxatomide (Celtect) is already available on the market. Furthermore, cetirizine and others are known as piperazine derivatives having antiallergic activity (Japanese Patent Publication S 63-11353). However, the antiallergic activity of these compounds is not fully satisfactory and a demand exists for compounds having more potent antiallergic activity.

In this state of the art the inventors of the present invention did synthetic and efficacy studies on related compounds. As a result, the inventors succeeded in synthesizing a series of novel benzylpiperazine derivatives and found that these derivatives have potent antiallergic and antiinflammatory activities. Based on these findings the inventors did further research and have perfected the present invention.

SUMMARY OF THE INVENTION

The present invention relates to:

(1) A benzylpiperazine derivative of formula (I) or a pharmacologically acceptable salt thereof (hereinafter referred to collectively as the compound of the invention)

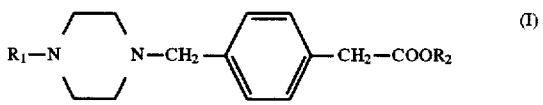
(I)

wherein $R_1$ represents a pyridine ring or a group of either formula (IV) or formula (V); $R_2$ represents hydrogen or lower alkyl.

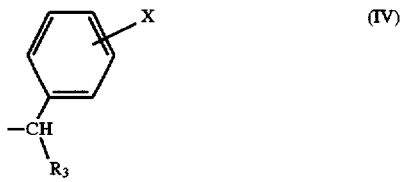
(IV)

wherein $R_3$ represents hydrogen, lower alkyl, a pyridine ring or a benzene ring which may be substituted by halogen; X represents halogen.

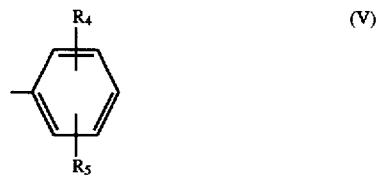
(V)

wherein $R_4$ and $R_5$ may be the same or different and each represents hydrogen, lower alkyl, lower alkoxy, halogen or carboxy;

(2) A process for producing the compound of the invention; and (3) An antiallergic composition and an antiinflammatory composition each comprising the piperazine derivative or pharmacologically acceptable salt defined in (1) above.

DETAILED DESCRIPTION OF THE INVENTION

Figure 1:
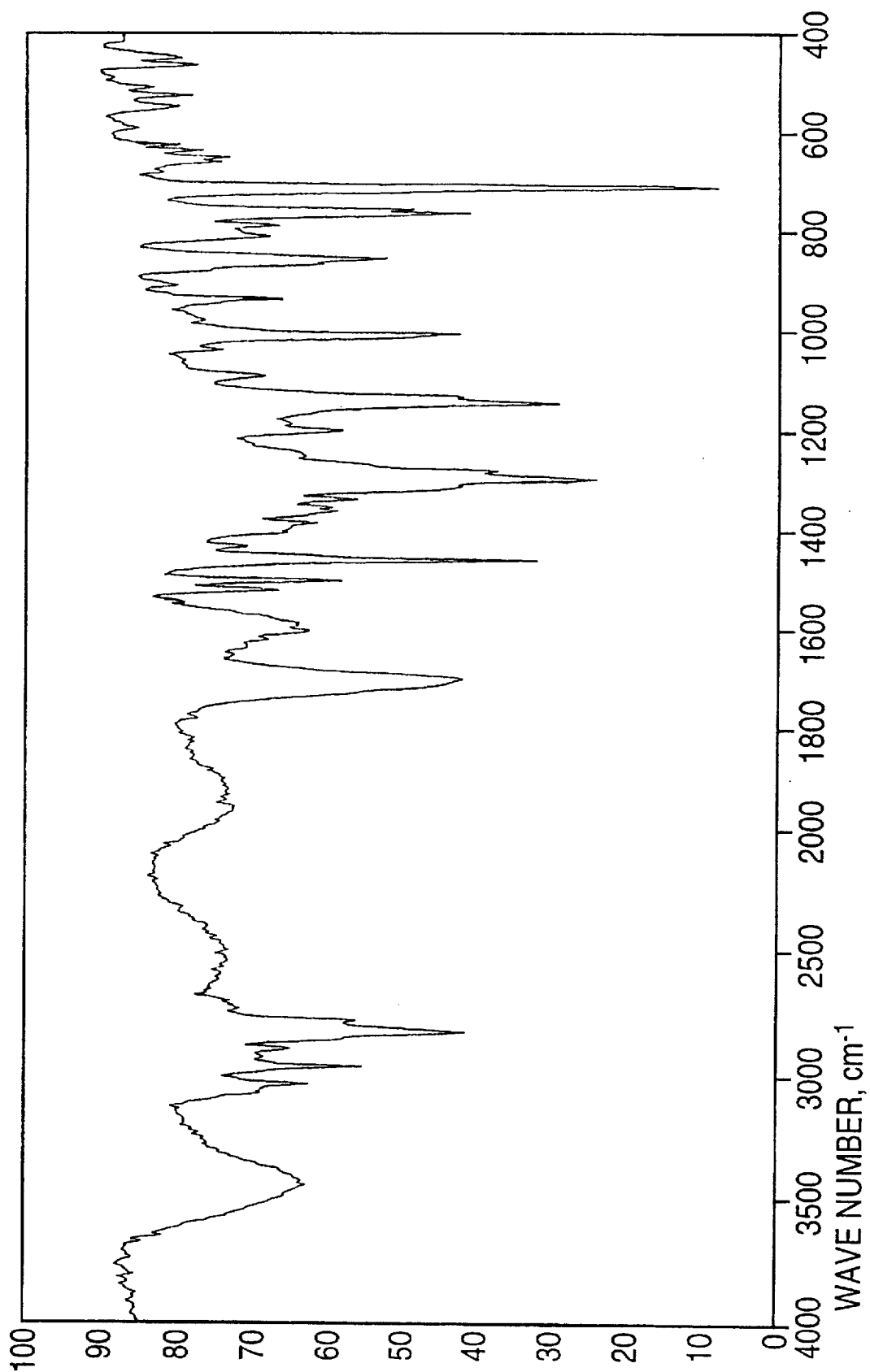
FIG. 1 shows an infrared absorption spectrum (IR) of 4-[(4-diphenylmethyl-1-piperazinyl)methyl]phenylacetic acid as synthesized in Example 1.

The compound of the present invention includes but is not limited to the following specific compounds and their pharmacologically acceptable salts.

(1) Methyl 4-[(4-diphenylmethyl-1-piperazinyl)methyl]phenylacetate (2) 4-[(4-Diphenylmethyl-1-piperazinyl)methyl]phenylacetic acid (3) 4-[[4-(2-Methoxyphenyl)-1-piperazinyl]-1-methyl]phenylacetic acid (4) 4-[[4-(2-Carboxyphenyl)-1-piperazinyl]methyl]phenylacetic acid (5) 4-[[4-(2-Pyridyl)-1-piperazinyl]methyl]phenylacetic acid (6) 4-[[4-(2-Toryl)-1-piperazinyl]methyl]phenylacetic acid (7) 4-[(4-Phenyl-1-piperazinyl)methyl]phenylacetic acid (8) 4-[[4-(2-Fluorophenyl)-1-piperazinyl]methyl]phenylacetic acid (9) 4-[[4-(2,5-Dimethylphenyl)-1-piperazinyl]methyl]phenylacetic acid

(10) 4-[[4-(4-Methoxyphenyl)-1-piperazinyl]methyl]phenylacetic acid

(11) 4-[[4-(3-Methoxyphenyl)-1-piperazinyl]methyl]phenylacetic acid

(12) 4-[[4-(3-trifluoromethylphenyl)-1-piperazinyl]methyl]phenylacetic acid

(13) Methyl 4-[[4-[phenyl-(2-pyridyl)methyl]-1-piperazinyl]methyl]phenylacetate

(14) 4-[[4-[phenyl-(2-pyridyl)methyl-1-piperazinyl]methyl]phenylacetic acid

(15) Methyl 4-[[4-[(4-chlorophenyl)phenylmethyl]-1-piperazinyl]methyl]phenylacetate

(16) 4-[[4-[(4-chlorophenyl)phenylmethyl]-1-piperazinyl]methyl]phenylacetate

The lower alkyl mentioned for $R_2$ in formula (I), $R_3$ in formula (IV), or $R_4$ and $R_5$ in formula (V) is a linear, branched, or cyclic alkyl group comprised of, preferably, 1–6 carbon atoms. Thus, methyl, ethyl, n-propyl, iso-propyl, cyclopropyl, n-butyl, tert-butyl, sec-butyl, n-pentyl, 1-ethylpropyl, isopentyl, etc. can be typically mentioned.

The lower alkoxy for $R_4$ and $R_5$ in formula (V) is a linear, branched, or cyclic alkoxy group comprised of, preferably, 1–6 carbon atoms. Thus, methoxy, ethoxy, propoxy, iso-propoxy, n-butoxy, iso-butoxy, tert-butoxy, n-pentyloxy, neopentyloxy, 2-methylbutoxy, 1,2-dimethylpropoxy, 1-ethylpropoxy, etc. can be typically mentioned.

Where $R_3$ in formula (IV) represents a benzene ring, the ring may be substituted by halogen. The halogen may be fluorine, chlorine, bromine, or iodine. The halogen mentioned for $R_4$ and $R_5$ in formula (V) has the same meaning as above.

The compound of formula (I) can be synthesized by reacting a piperazine derivative of formula (II) [wherein $R_1$ is as defined hereinbefore| with a 4-halomethylphenylacetic acid ester of formula (III) |wherein $R_2$ is as defined hereinbefore; X represents the halogen defined hereinbefore|. The process for synthesizing the compound of the invention is now described in detail.

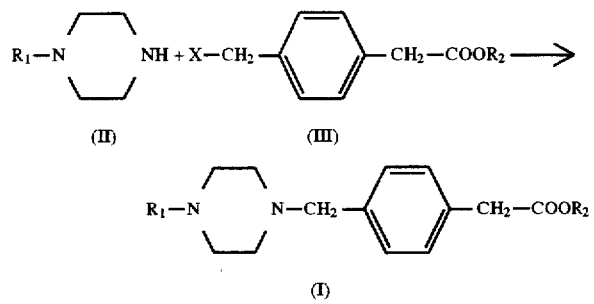

The starting piperazine derivative of formula (II) may be purchased from a commercial source or, if desired, can be synthesized by known technology, e.g. whichever of the following alternative processes. Thus, as shown in the following reaction schema, the compound (II) can be synthesized by reacting a halobenzene derivative with either piperazine or N-benzylpiperazine in the presence of an alkali carbonate either in an organic solvent or in the absence of a solvent under heating and where N-benzylpiperazine was used, further conducting a catalytic reduction reaction using palladium-on-carbon (Pd-C). In the reaction schema, $R_4$, $R_5$ and X have the same meanings as defined hereinbefore.

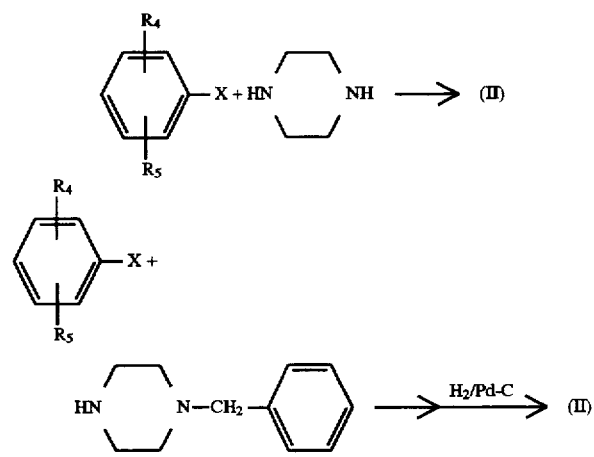

In the alternative process shown in the following reaction schema, the compound (II) can be synthesized by reacting an aniline derivative with a hydrohalic acid salt of bis (dihaloethyl)amine either in an organic solvent or in the absence of a solvent under heating. In the reaction schema, $R_4$, $R_5$, and X have the same meanings as defined hereinbefore.

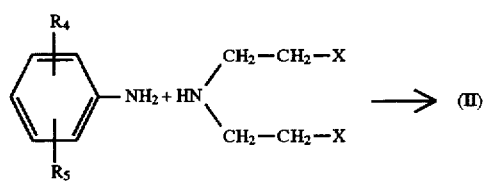

The mating 4-halomethylphenylacetic acid ester of formula (III) may be a commercial product or, if desired, can be synthesized by known production technology, for example in the following manner. Thus, a halomethylphenylacetic acid and a lower alcohol are heated together in the presence of sulfuric acid or hydrogen chloride in dichloroethane. In this reaction schema, $R_2$ and X are as defined hereinbefore.

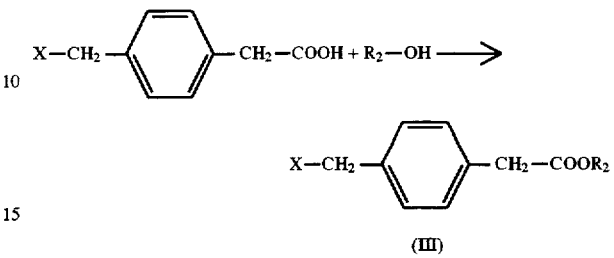

The compounds (II) and (III) prepared as above are reacted with each other in the presence of an organic amine, such as triethylamine, in an inert solvent, such as dioxane, at room temperature for several hours, whereby the compound (I) of the invention can be obtained. The preferred solvent for use in this reaction is dioxane but any other solvent that does not interfere with the reaction can be employed. The preferred organic amine is triethylamine or tributyl amine. The solvent is then distilled off under reduced pressure and the residue is extracted with ethyl acetate or the like. The crystals thus obtained are recrystallized from a suitable solvent such as methanol to provide the ester of the compound of the invention in high yield.

The ester thus obtained is saponified (hydrolyzed) with an alkali, e.g. sodium hydroxide or potassium hydroxide, in an alcohol or an aqueous solution of alcohol at room temperature or under warming for a few hours. The solvent is then distilled off and the residue is dissolved in water. The solution is neutralized with an acid, e.g. acetic acid, and the resulting crystals are harvested by filtration. This crystal crop is recrystallized from a suitable solvent, e.g. methanol-water, to provide the free compound of the invention in high yield.

The compound (I) of the invention as synthesized in the above manner can be isolated in the form of a pharmacologically acceptable salt. For example, the objective salt can be obtained by adding an alkali metal or alkaline earth metal ion donor, e.g. the hydroxide, carbonate or hydrogencarbonate of the corresponding metal to the free compound in a suitable solvent. This conversion to the salt can be carried out either after isolation of the free compound from the reaction mixture or without prior isolation.

The compound of the invention as obtained in the above manner is a novel compound never heretofore described in the literature and is of great value in that it has excellent antiallergic and antiinflammatory activities.

The compound of the invention for use in the antiallergic or antiinflammatory composition of the present invention can be whichever of its free form and a pharmacologically acceptable salt thereof. The pharmacologically acceptable salt includes but is not limited to salts with alkali metals, e.g. sodium, potassium, etc., or alkaline earth metals, e.g. calcium, magnesium, etc. Aside from the above salts, inorganic salts, such as the hydrochloride, sulfate, nitrate, etc. and organic salts such as the acetate, maleate, tartarate, etc. can also be mentioned by way of example. Even other salts can also be used only if they are pharmacologically acceptable.

The allergic disease that can be treated with the antiallergic composition of the present invention includes bronchial asthma, pollinosis, allergic rhinitis, dietary allergic gastritis, allergic diarrhea, ulcerative colitis, stomatitis, periarteritis nodosa, obliterating endarteritis, endocarditis, urticaria, eczema, contact dermatitis, phlyctena, sympathetic ophthalmia, allergic conjunctivitis, allergic keratitis, etc.

The inflammatory disease that can be treated with the antiinflammatory composition of the present invention includes hemorrhoidal disease, rheumatoid arthritis, rheumatoid deformans, spondylitis deformans, osteoarthritis, lumbago, celiagra, acute tympanitis, cystitis, prostatitis, dentalgia, uveitis, sinusitis, etc.

The antiallergic composition and antiinflammatory composition of the present invention are put to use orally or otherwise in a suitable manner for the treatment of the above-mentioned diseases. As to dosage forms, solid preparations such as tablets, granules, powders, capsules, ointments, etc. and liquid preparations such as ophthalmic, nasal and otic preparations, syrups, etc. can be manufactured each by the established pharmaceutical manufacturing procedure. In the manufacture of such dosage forms, the conventional excipients, binders, disintegrators, thickeners, dispersants, reabsorption promoters, buffers, surfactants, preservatives, isotonizing agents, stabilizers, pH control agents and other additives can be selectively employed.

The dosage of the compound of the invention in its application in the form of an antiallergic composition or an antiinflammatory composition is dependent on the species of compound, type of disease to be treated, patient's body weight and age, indications, and therapeutic regimen, etc. Taking an injection as an example, the recommended dosage for an adult human is about 0.1 mg–about 30 mg/day. For oral administration, about 1 mg–about 100 mg per dose can be administered a few times a day for an adult human. For use as eye-drops, a few drops of a solution or suspension of about 0.01 (w/v) %–0.5 (w/v) % concentration can be advantageously instilled several times a day.

In the antiallergic composition and antiinflammatory composition of the present invention, more than one species of the compound of this invention can be used in a suitable combination, where necessary.

EXAMPLES

The following examples and formulation examples illustrate the present invention in further detail.

Example 1

4-[(4-Diphenylmethyl-1-piperazinyl)methyl]phenylacetic acid

A 200 ml eggplant-shaped flask was charged with 5.38 g of methyl 4-bromomethylphenylacetate, 6.06 g of 1-benzhydrylpiperazine, 6.1 ml of triethylamine, and 100 ml of dioxane and the mixture was stirred at room temperature for 5 hours. The solvent was then distilled off and the residue was extracted with ethyl acetate. The extract was washed with water, the solvent was distilled off, and the residue was recrystallized from methanol to provide 8.33 g of methyl 4-[(4-diphenylmethyl-1-piperazinyl)methyl]phenylacetate melting at 124° C.–125° C.

Elemental analysis for $C_{27}H_{30}N_2O_2$
Calcd. (%): C, 78.23; H, 7.29; N, 6.76
Found (%): C, 77.98; H, 7.13; N, 6.60

The compound thus obtained, 2 g, was added to a mixture of 10 ml methanol and 50 ml 2N-sodium hydroxide solution and the mixture was refluxed for 3 hours. The solvent was then distilled off and the residue was dissolved in water and filtered. The filtrate was neutralized with acetic acid and the resulting crystals were harvested by filtration. This crystal crop was dissolved in 2N-hydrochloric acid and the solution was filtered to remove insolubles. The filtrate was neutralized with aqueous sodium hydroxide solution and the resulting crystals were harvested by filtration and recrystallized from methanol-water to provide 1.25 g of the title compound melting at 183° C.–185° C. The IR absorption spectrum of this product is shown in FIG. 1.

Elemental analysis for $C_{26}H_{28}N_2O_2$
Calcd. (%): C, 77.97; H, 7.05; N, 6.99
Found (%): C, 77.80; H, 6.97; N, 6.96

Example 2

4-[[4-(2-Methoxyphenyl)-1-piperazinyl]methyl] phenylacetic acid

Figure 2:
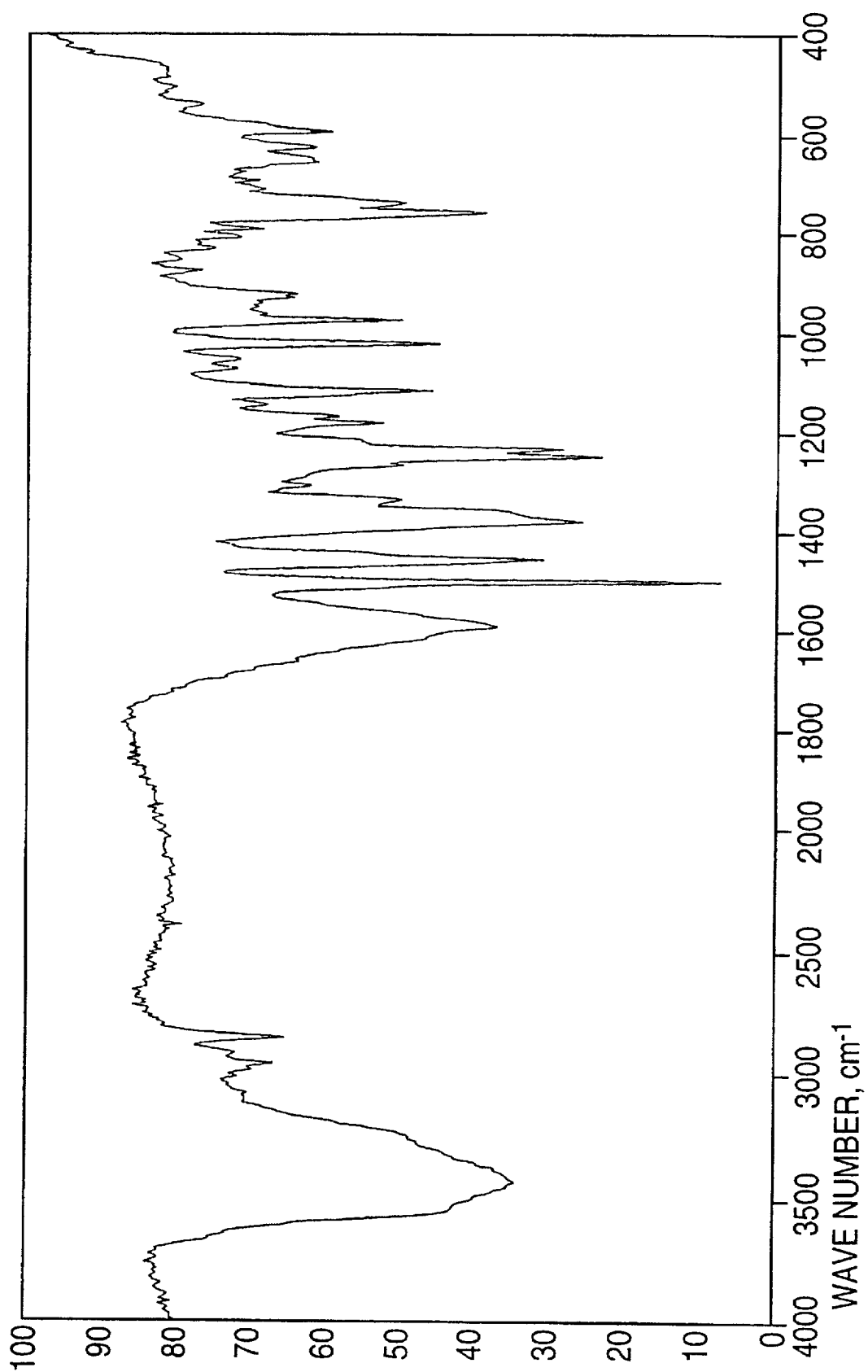
FIG. 2 shows an infrared absorption spectrum (IR) of 4-[[4-(2-methoxyphenyl)-1-piperazinyl]methyl]phenylacetic acid as synthesized in Example 2.

In triethylamine (3 ml)-dioxane (80 ml) were dissolved 2.4 g of methyl 4-bromomethylphenylacetate and 1.9 g of 1-(2-methoxyphenyl)piperazine and the solution was stirred at room temperature for 4 hours. The solvent was then distilled off and the residue was extracted with ethyl acetate. The extract was washed with water and dried over anhydrous sodium sulfate, and the solvent was distilled off. The residue was purified by column chromatography [silica gel, hexane-ethyl acetate=2:1] and the resulting oil was refluxed in a mixture of 30 ml 2N-sodium hydroxide and 10 ml methanol for 3 hours. The solvent was then distilled off and the residue was dissolved in water and filtered. The filtrate was neutralized with acetic acid and extracted with chloroform. The solvent was then distilled off and the residue was recrystallized from methanol-ethylether to provide 2.0 g of the title compound melting at 87° C.–90° C. The IR absorption spectrum of this product is presented in FIG. 2.

Elemental analysis for $C_{20}H_{24}N_2O_3 \cdot 1.0\ H_2O$
Calcd. (%): C, 67.02; H, 7.31; N, 7.82
Found (%): C, 67.19; H, 7.46; N, 7.70

Example 3

4-[[4-(2-Carboxyphenyl)-1-piperazinyl]methyl] phenylacetic acid

Using 2.4 g of methyl 4-bromomethylphenylacetate, 2.9 g of ethyl 2-piperazinylbenzoate acetate, 3 ml of triethylamine, and 80 ml of dioxane, the reaction procedure of Example 2 was otherwise repeated and the reaction product was recrystallized from ethanol-water to provide 2.0 g of the title compound melting at 179° C.–181° C.

Elemental analysis for $C_{20}H_{22}N_2O_4 \cdot 0.5\ H_2O$
Calcd. (%): C, 66.10; H, 6.38; N, 7.71
Found (%): C, 66.25; H, 6.64; N, 7.64

Example 4

4-[[4-(2-Pyridyl)-1-piperazinyl]methyl]phenylacetic acid hydrochloride

Using 2.2 g of methyl 4-bromomethylphenylacetate, 1.5 g of 1-(2-piperazinyl)piperazine, 1.9 ml of triethylamine, and 70 ml of dioxane, the reaction procedure of Example 2 was otherwise repeated and the reaction product was converted to the hydrochloride using 2N-hydrochloric acid and recrystallized from ethanol-ether to provide 1.1 g of the title compound melting at 214° C.–216° C.

Elemental analysis for $C_{18}H_{21}N_3O_2 \cdot HCl \cdot 1.25\ H_2O$
Calcd. (%): C, 58.37; H, 6.33; N, 11.35
Found (%): C, 58.39; H, 6.27; N, 11.29

Example 5

4-||4-(2-Tolyl)-1-piperazinyl|methyl|phenylacetic acid hydrochloride

Using 2.2 g of methyl 4-bromomethylphenylacetate, 1.9 g of 1-(2-tolyl)piperazine hydrochloride, 2.5 ml of triethylamine, and 80 ml of dioxane, the reaction procedure of Example 2 was otherwise repeated and the reaction product was converted to the hydrochloride using 2N-hydrochloric acid and recrystallized from ethanol-ether to provide 1.7 g of the title compound melting at 249° C.–252° C.

Elemental analysis for $C_{20}H_{24}N_2O_2 \cdot HCl \cdot 1.75\ H_2O$

Calcd. (%): C, 61.22; H, 7.32; N, 7.14

Found (%): C, 61.19; H, 6.90; N, 7.11 [0046]

Example 6

4-|(4-Phenyl-1-piperazinyl)methyl]phenylacetic acid hydrochloride

Using 2.3 g of methyl 4-bromomethylphenylacetate, 2.0 g of 1-phenylpiperazine, 2 ml of triethylamine, and 80 ml of dioxane, the reaction procedure of Example 2 was otherwise repeated and the reaction product was converted to the hydrochloride using 2N-hydrochloric acid and recrystallized from methanol-ether to provide 2.0 g of the title compound melting at 231° C.–234° C.

Elemental analysis for $C_{19}H_{22}N_2O_2 \cdot HCl \cdot 1.5\ H_2O$

Calcd. (%): C, 61.04; H, 7.01; N, 7.49

Found (%): C, 61.04; H, 6.72; N, 7.47

Example 7

4-[[4-(2-Fluorophenyl)-1-piperazinyl]methyl]phenylacetic acid hydrochloride

In 50 ml of methanol was suspended 3.4 g of 4-bromomethylphenylacetic acid followed by dropwise addition of 2.1 ml triethylamine to prepare a homogeneous solution. Then, a solution of 2.7 g 1-(2-fluorophenyl)piperazine in 50 ml methanol was added dropwise to the above solution. Thereafter, 2 ml of triethylamine was further added dropwise and the mixture was stirred at room temperature for 30 minutes and then refluxed for 2 hours. The solvent was then distilled off and the residue was dissolved in water. The insoluble matter was filtered off and the filtrate was neutralized with acetic acid and extracted with chloroform. The solvent was distilled off and the residue was treated with 2N-hydrochloric acid. The resulting hydrochloride was recrystallized from acetone to provide 3.0 g of the title compound melting at 253° C.–255° C.

Elemental analysis for $C_{19}H_{21}N_2O_2F \cdot HCl \cdot 0.25\ H_2O$

Calcd. (%): C, 61.79; H, 6.14; N, 7.58

Found (%): C, 61.85; H, 5.93; N, 7.47

Example 8

4-[[4-(2,5-Dimethylphenyl-1-piperazinyl]methyl] phenylacetic acid hydrochloride

Using 3.4 g of 4-bromomethylphenylacetic acid, 2.9 g of 2,5-dimethylphenylpiperazine, 5 ml of triethylamine, and 100 ml of methanol, the reaction procedure of Example 7 was otherwise repeated and the reaction product was recrystallized from ethanol-water to provide 2.3 g of the title compound melting at 260° C.–261° C.

Elemental analysis for $C_{21}H_{26}N_2O_2 \cdot HCl \cdot 0.25\ H_2O$

Calcd. (%): C, 66.48; H, 7.31; N, 7.38

Found (%): C, 66.71; H, 7.26; N, 7.36

Example 9

4-||4-(4-Methoxyphenyl-1-piperazinyl|methyl|phenylacetic acid dihydrochloride

Using 3.4 g of 4-bromomethylphenylacetic acid, 2.9 g of 1-(4-methoxyphenyl)piperazine, 5 ml of triethylamine, and 100 ml of ethanol, the reaction procedure of Example 7 was otherwise repeated and the reaction product was recrystallized from ethanol-ether to provide 2.4 g of the title compound melting at 225° C.–230° C.

Elemental analysis for $C_{20}H_{24}N_2O_3 \cdot 2\ HCl$

Calcd. (%): C, 58.12; H, 6.34; N, 6.78

Found (%): C, 58.06; H, 6.38; N, 6.73

Example 10

4-||4-(3-Methoxyphenyl)-1-piperazinyl|methyl|phenyl acetic acid dihydrochloride

Using 2.3 g of 4-bromomethylphenylacetic acid, 1.9 g of 1-(3-methoxyphenyl)piperazine, 3 ml of triethylamine, and 100 ml of methanol, the reaction procedure of Example 7 was otherwise repeated and the reaction product was recrystallized from ethanol-ether to provide 1.6 g of the title compound melting at 176° C.–179° C.

Elemental analysis for $C_{20}H_{24}N_2O_3 \cdot 2\ HCl \cdot 0.25\ H_2O$

Calcd. (%): C, 57.49; H, 6.39; N, 6.70

Found (%): C, 57.76; H, 6.35; N, 6.80

Example 11

4-[[4-(3-trifluoromethyl)-1-piperazinyl]methyl] phenylacetic acid hydrochloride

Using 2.4 g of 4-bromomethylphenylacetic acid, 2.3 g of 1-(3-trifluoromethyl)phenylpiperazine, 1.7 ml of triethylamine, and 100 ml of dioxane, the reaction procedure of Example 2 was otherwise repeated and the reaction product was converted to the hydrochloride using 2N-hydrochloric acid and recrystallized from methanol-acetone to provide 2.3 g of the title compound melting at 173° C.–175° C.

Elemental analysis for $C_{20}H_{21}N_2O_2F_3 \cdot HCl \cdot 1.25\ H_2O$

Calcd. (%): C, 54.92; H, 5.65; N, 6.40

Found (%): C, 54.72; H, 5.38; N, 6.15

Example 12

4-[[4-[Phenyl-(2-pyridyl)methyl]-1-piperazinyl]methyl] phenylacetic acid trihydrochloride Using 2.8 g of methyl 4-bromomethylphenylacetate, 2.9 g of 1-[phenyl-(2-pyridyl)methyl]piperazine, 2 ml of triethylamine, and 100 ml of dioxane, the reaction procedure of Example 1 was otherwise repeated and recrystallized from benzene-hexane to provide 2.47 g of methyl 4-[[4-[phenyl-(2-pyridyl)methyl]-1-piperazinyl]methyl] phenylacetate melting at 122° C.–123° C.

Elemental analysis for $C_{26}H_{29}N_3O_2$

Calcd. (%): C, 75.15; H, 7.03; N, 10.11

Found (%): C, 74.87; H, 7.05; N, 10.07

The compound thus obtained, 1.0 g, was hydrolyzed in the same manner as in Example 1 and converted to the hydrochloride using 2N-hydrochloric acid and recrystallized from acetone to provide 0.8 g of the title compound melting 193° C.–195° C.

Elemental analysis for $C_{25}H_{27}N_3O_2 \cdot 3\ HCl \cdot H_2O$

Calcd. (%): C, 56.77; H, 6.10; N, 7.94

Found (%): C, 56.69; H, 6.15; N, 7.62

Example 13

4-||4-|4-chlorophenylmethyl|-1-piperazinyl|methyl| phenylacetic acid

Using 2.4 g of 4-bromomethylphenylacetic acid, 2.9 g of 1-|(4-chlorophenyl)phenylmethyl|piperazine, 2.8 ml of triethylamine, and 100 ml of dioxane, the reaction procedure of Example 1 was otherwise repeated and recrystallized from benzene-hexane to provide 1.8 g of methyl 4-||4-|(4-chlorophenyl)phenylmethyl|-1-piperazinyl|methyl| phenylacetate melting at 113° C.–115° C.

Elemental analysis for $C_{27}H_{29}N_2O_2Cl$

Calcd. (%): C, 72.23; H, 6.51; N, 6.24
Found (%): C, 72.28; H, 6.33; N, 6.12

The compound thus obtained, 1.8 g, was hydrolyzed in the same manner as in Example 1 and recrystallized from isopropylalcohol to provide 1.5 g of the title compound having amorphous crystals.

Elemental analysis for $C_{26}H_{27}N_2O_2Cl \cdot 1.5\ H_2O$

Calcd. (%): C, 67.60; H, 6.55; N, 6.06
Found (%): C, 67.52; H, 6.52; N, 5.72

Example 14

Effect of the compound of the invention as administered orally on rat back passive cutaneous anaphylactic (PCA) reaction The effect of the compound of the invention as administered orally on rat back passive cutaneous anaphylactic reaction was investigated.

[Method]

Sixty (60) male Wistar rats (body weights ca 100 g), purchased from SLC, were used. Under pentobarbital anesthesia, 100 μl of antiserum (16-fold dilution) was injected subcutaneously at the back of rats and 48 hr later 5 ml/kg of a mixture of ovalbumin (25 mg/kg) and Evans blue (12.5 mg/kg) was injected intravenously to induce a PCA reaction.

Thirty (30) minutes after induction of the PCA reaction, the rats were sacrificed and the dorsal skin area showing dye leaks was excised and extracted with 6 ml of formamide. The absorbance (625 nm) of the extract was measured.

The test material was administered orally 60 minutes before induction of the PCA reaction.

[Results]

The results are shown in Tables 1 and 2.

TABLE 1

Effect of oral administration of the compound of the invention on rat back PCA reaction

| Test material | Dose (mg/kg) | Absorbance (Abs.) | Inhibition rate (%) |
|---|---|---|---|
| 0.5% CMC | — | 0.438 ± 0.048 | — |
| Compound of Example 1 | 30 | 0.128 ± 0.041* | 70.8 |

Each value represents mean ± S.D. (n = 5).
Significance of difference from the control (CMC) group: *; p < 0.01.
CMC: carboxymethylcellulose

TABLE 2

Effect of oral administration of the compound of the invention on rat back PCA reaction

| Test material | Dose (mg/kg) | Inhibition rate (%) |
|---|---|---|
| Compound of Example 2 | 30 | 60.5** |
| Compound of Example 5 | 30 | 57.3** |
| Compound of Example 6 | 30 | 19.5* |
| Compound of Example 7 | 30 | 23.8** |
| Compound of Example 9 | 30 | 22.5** |
| Ester Compound of Example 12 | 30 | 49.0** |
| Free Compound of Example 12 | 30 | 38.2** |

Each value represents mean ± S.D. (n = 6–7).
Significance of difference from the control (CMC) group: *; p < 0.05, **; p < 0.01.

It is apparent from Table 1 that oral administration of the compound of Example 1, 30 mg/kg, resulted in a significant (70.8%) inhibition of PCA reaction. It is also apparent from Table 2 that the compounds of Examples 2, 5, 6, 7, 9 and 12 also have significant antiallergic actions. These results indicate that the compound of the invention is of value as an antiallergic agent.

Example 15

Effect of oral administration of the compound of the invention on rat conjunctival passive cutaneous anaphylactic reaction The effect of oral administration of the compound of the invention on rat conjunctival passive cutaneous anaphylactic (PCA) reaction was investigated.

[Method]

Nineteen (19) male Wistar rats (body weights ca 100 g), purchased from SLC, were used.

Under pentobarbital anesthesia, 50 μl of antiserum (8-fold dilution) was injected subconjunctivally in the rat palpebra and 48 hr later 5 ml/kg of a mixture of ovalbumin (25 mg/kg) and Evans blue (12.5 mg/kg) was injected intravenously to induce a PCA reaction.

Thirty (30) minutes after induction of the PCA reaction, the rats were sacrificed and the palpebral conjunctival area showing dye leaks was excised and extracted with 3 ml of formamide. The absorbance (625 nm) of the extract was measured.

The test material was administered orally 60 minutes before induction of the PCA reaction.

[Results]

The results are shown in Table 3.

TABLE 3

Effect of oral administration of the compound of the invention on rat conjunctival PCA reaction

| Test material | Dose (mg/kg) | Absorbance (Abs.) | Inhibition rate (%) |
|---|---|---|---|
| 0.5% CMC | — | 0.611 ± 0.276 | — |
| Compound of Example 1 | 10 | 0.212 ± 0.032* | 65.3 |
| | 30 | 0.128 ± 0.046* | 79.1 |
| | 100 | 0.104 ± 0.052* | 83.0 |

Each value represents mean ± S.D. (n = 4–5).
Significance of difference from the control (CMC) group: *; p < 0.01.

It is apparent from Table 3 that 10, 30, and 100 mg/kg p.o. of the compound of the invention did significantly and dose-dependently inhibit the conjunctival PCA reaction, by 65.3%, 79.1%, and 83.0%, respectively. The above results indicate the usefulness of the compound of the invention as an antiallergic agent.

Example 16

The effect of the compound of the invention as administered topically on rat conjunctival PCA reaction The effect of the compound of the invention as administered topically on rat conjunctival PCA reaction was investigated.

[Method]

Twenty-three (23) male Wistar rats (body weights ca 100 g), purchased from SLC, were used.

To rats under pentobarbital anesthesia, 50 μl of antiserum (8-fold dilution) was injected subconjunctivally in the palpebra and 48 hours later 5 ml/kg of a mixture of ovalbumin (25 mg/kg) and Evans blue (12.5 mg/kg) was injected intravenously to induce PCA reaction in the palpebral conjunctiva.

The animals were sacrificed 30 minutes after induction of the PCA reaction and the palpebral conjunctival area showing dye leaks was excised and extracted with 3 ml of formamide and the absorbance (625 nm) was measured.

The test sample, 10 μl, was instilled in the eye 30 and 60 minutes before induction of PCA reaction.

[Results]

The results are presented in Table 4.

TABLE 4

Effect of the compound of the invention as administered topically on rat conjunctival PCA reaction

| Test material | Concentration (%) | Absorbance (Abs.) | Inhibition rate (%) |
|---|---|---|---|
| Physiological saline | — | 0.509 ± 0.073 | — |
| Compound of Example 1 | 0.125 | 0.409 ± 0.128 | 19.6 |
|  | 0.25 | 0.350 ± 0.132* | 31.2 |
|  | 0.5 | 0.293 ± 0.030** | 42.4 |

Each value represents mean ± S.D. (n = 5–6).
Significance of difference from control (saline) group: *; $p < 0.05$, **; $p < 0.01$.

It is apparent from Table 4 that the compound of the invention inhibited conjunctival PCA reaction dose-dependently, i.e. 19.6%, 31.2%, and 42.4% at concentrations of 0.125%, 0.25%, and 0.5%, respectively. These results indicate the usefulness of the compound of the invention as an antiallergic ophthalmic solution.

Example 17

Effect of the compound of the invention as administered orally on rat histamine-induced inflammation The effect of the compound of the invention as administered orally on rat histamine-induced inflammation was investigated.

[Method]

Fifty-seven (57) male Wistar rats (body weights ca 100 g), purchased from SLC, were used.

To rats, 50 mg/5 ml/kg of Evans blue was injected intravenously and immediately then 50 μl of 0.1% histamine diphosphate solution was injected intradermally at the back to induce histamine inflammation.

The rats were sacrificed 30 minutes after induction of histamine inflammation, the dorsal skin area showing dye leaks was excised and extracted with 5 ml of formamide. The absorbance (625 nm) of the extract was measured.

The test sample was administered orally 60 minutes before induction of histamine inflammation.

[Results]

The results are presented in table 5.

TABLE 5

Effect of the compound of the invention as administered orally on rat histamine-induced inflammation

| Test material | Dose (mg/kg) | Absorbance (Abs.) | Inhibition rate (%) |
|---|---|---|---|
| 0.5% CMC | — | 1.629 ± 0.353 | — |
| Compound of Example 1 | 0.3 | 0.479 ± 0.076* | 70.6 |
|  | 1 | 0.255 ± 0.066* | 84.3 |
|  | 3 | 0.200 ± 0.122* | 87.7 |
| 0.5% CMC | — | 0.914 ± 0.293 | — |
| Compound of Example 2 | 3 | 0.734 ± 0.201 | 19.7 |
|  | 10 | 0.586 ± 0.177* | 35.9 |
|  | 30 | 0.347 ± 0.071* | 62.0 |
|  | 100 | 0.316 ± 0.104* | 65.4 |

Each value represents meant ± S.D. (n = 5–7).
Significance of difference from the control (CMC) group: *; $p < 0.01$.

It is apparent from Table 5 that oral administration of the compound of Example 1 inhibited histamine-induced inflammation dose-dependently, i.e. 70.6%, 84.3%, and 87.7% at the dose levels of 0.3, 1, and 3 mg/kg, respectively. It can also be seen that the compound of Example 2 inhibited histamine-induced inflammation dose-dependently, i.e. 19.7%, 35.9%, 62.0%, and 65.4% at the doses of 3, 10, 30, and 100 mg/kg, respectively. The above results indicate that the compound of the invention is of value as an antiallergic agent.

Example 18

Effect of the compound of the invention as administered topically on histamine-induced palpebral conjunctival edema in rats The effect of the compound of the invention as administered topically on histamine-induced palpebral conjunctival edema in rats was investigated.

[Method]

Nineteen (19) male Wistar rats (body weights ca 100 g), purchased from SLC, were used.

To rats under pentobarbital anesthesia, 50 μl of 0.1% histamine diphosphate solution was injected subconjunctivally in the palpebra to induce palpebral conjunctival edema.

The rats were sacrificed one hour after histamine injection and the edematous portion of the lid was excised and weighed (mg).

The test sample, 10 μl per dose, was administered 30 and 60 minutes before subconjunctival histamine injection.

[Results]

The results are presented in Table 6.

TABLE 6

Effect of the compound of the invention as administered topically on histamine-induced palpebral conjunctival edema in rats

| Test material | Concentration (%) | Edema weight (mg) | Inhibition rate (%) |
|---|---|---|---|
| Physiological saline | — | 47.8 ± 11.4 | — |
| Compound of Example 1 | 0.125 | 29.6 ± 8.4* | 38.1 |
|  | 0.25 | 24.4 ± 6.1* | 49.0 |
|  | 0.5 | 15.8 ± 4.5* | 66.9 |

Each value represents mean ± S.D. (n = 4–5).
Significance of difference from control (saline) group: *; $p < 0.01$.

It is apparent from Table 6 that instillation of the compound of the invention inhibited palpebral conjunctival edema significantly, i.e. 38.1%, 49.0%, and 66.9% at concentrations of 0.125%, 0.25%, and 0.5%, respectively. The results indicate that the compound of the invention provides a useful antiallergic ophthalmic solution.

Example 19

Effect of the compound of the invention on DNFB (dinitrofluorobenzene)-induced contact dermatitis The effect of the compound of the invention on DNFB-induced contact dermatitis was investigated.

[Method]

Thirty-one (31) 8-week-old male C57BL/6J mice, purchased from Clea Japan, were used.

A 0.5% solution of DNFB in acetone, 30 μl, was applied to the abdominal skin area of the mouse which had been clipped of hairs for sensitization. Five (5) days after the sensitization, 50 μl of a 0.1% solution of DNFB in acetone was applied to the inner and outer surfaces of the right auricle of the mouse for challenge. Then, 24 hours later, the thickness of the right auricle was measured with a dial thickness gauge and the edema rate (%) was calculated with reference to the pre-challenge thickness.

The test sample, 50 μl, was applied to the inner and outer surfaces of the right auricle of the mouse 60 minutes before challenge.

[Results]

The results are presented in Table 7.

TABLE 7

Effect of the compound of the invention on DNFB-induced contact dermatitis

| Test material | Concentration (%) | Edema rate (%) | Inhibition rate (%) |
|---|---|---|---|
| Methanol | — | 86.8 ± 18.6 | — |
| Compound of Example 1 | 0.125 | 42.3 ± 7.0* | 51.2 |
|  | 0.25 | 38.2 ± 12.2* | 56.0 |
|  | 0.5 | 35.5 ± 7.9* | 59.1 |
| Indomethacin | 1.0 | 21.9 ± 6.9* | 74.8 |

Each value represents mean ± S.D. (n = 6–7).
Significance of difference from control (methanol) group: *; p < 0.01.

It is apparent from Table 7 that the compound of the invention inhibited DNFB-induced ear edema significantly, i.e. 51.2%, 56.0%, and 59.1% at concentrations of 0.125%, 0.25%, and 0.5%, respectively. Indomethacin also inhibited the edema significantly, i.e. 74.8% at 1.0% concentration. The above results indicate that the compound of the invention is useful for the treatment of contact dermatitis.

Example 20

Effect of the compound of the invention on arachidonic acid-induced ear edema

The effect of the compound of the invention on arachidonic acid-induced ear edema was investigated.

[Method]

Twenty-five (25) 5-week-old male ICR mice, purchased from SLC, were used.

A solution (12.5 mg/ml) of arachidonic acid in acetone, 10 μl, was evenly applied to the outer and inner surfaces of the right auricle of the mouse to induce ear edema. One (1) hour after induction of ear edema, the thickness of the right auricle of the mouse was measured with a dial thickness gauge and the edema rate was calculated with respect to the thickness before induction of edema.

The test sample, 20 μl, was applied to the outer and inner surfaces of the auricle 30 minutes before induction of edema.

[Results]

The results are presented in Table 8.

TABLE 8

Effect of the compound of the invention on arachidonic acid-induced ear edema

| Test material | Concentration (%) | Edema rate (%) | Inhibition rate (%) |
|---|---|---|---|
| Methanol | — | 60.7 ± 14.0 | — |
| Compound of Example 1 | 0.25 | 49.0 ± 9.4 | 19.3 |
|  | 0.5 | 24.5 ± 13.5* | 59.6 |
| Indomethacin | 1.0 | 17.2 ± 14.8* | 71.7 |

Each value represents mean ± S.D. (n = 6–7).
Significance of difference from control (methanol) group: *; p < 0.01.

It is apparent from Table 8 that a 0.5% methanolic solution of the compound of the invention inhibited arachidonic acid-induced ear edema significantly or 59.6%. On the other hand, 1.0% indomethacin (dissolved in methanol) also inhibited the edema by 71.7%. These findings indicate that the compound of the invention is a useful antiinflammatory agent.

Example 21

Effect of the compound of the invention as administered orally on carrageenin-induced foot edema in rats The effect of the compound of the invention as administered orally on carrageenin-induced foot edema in rats was investigated.

[Method]

Thirty-seven (37) 4-week-old male SD rats, purchased from SLC, were used.

A 1% solution of λ-carrageenin, 0.1 ml, was injected subcutaneously at the footpad of the right hind paw to induce foot edema. The foot volume was measured 2 hours after carrageenin injection and the edema rate (%) was calculated.

The test sample was administered orally one hour before carrageenin injection.

[Results]

The results are shown in Tables 9 and 10.

TABLE 9

Effect of the compound of the invention as administered orally on carrageenin-induced foot edema in rats

| Test material | Dose (mg/kg) | Edema rate (%) | Inhibition rate (%) |
|---|---|---|---|
| 0.5% CMC | — | 58.2 ± 16.5 | — |
| Compound of Example 2 | 100 | 27.3 ± 7.2* | 53.0 |
| Indomethacin | 30 | 37.9 ± 11.0* | 34.8 |

Each value represents mean ± S.D. (n = 6–7).
Significance of difference from control (CMC) group: *; p < 0.01.

TABLE 10

Effect of the compound of the invention as administered orally on carrageenin-induced foot edema in rats

| Test material | Dose (mg/kg) | Inhibition rate (%) |
|---|---|---|
| Compound of Example 5 | 100 | 39.3** |
| Compound of Example 6 | 100 | 16.6* |
| Compound of Example 7 | 100 | 42.7** |

Each value represents mean ± S.D. (n = 6).
Significance of difference from control (CMC) group: *; p < 0.05, **; p < 0.01.

It is apparent from Table 9 that the compound of Example 2, administered orally in a dose of 100 mg/kg, inhibited carrageenin-induced foot edema significantly, i.e. by 53.0%. It is apparent from Table 10 that the compounds of Examples 5, 6, and 7 also inhibited foot edema significantly. On the other hand, indomethacin in an oral dose of 30 mg/kg caused a significant, i.e. 34.8%, inhibition of foot edema. The above findings indicate that the compound of the invention is a useful antiinflammatory agent.

Formulation Example 1

Oral Tablets

| | |
|---|---|
| 4-[(4-Diphenylmethyl-1-piperazinyl)methyl]phenylacetic acid | 30 mg |
| Lactose | 80 mg |
| Starch | 17 mg |
| Magnesium stearate | 3 mg |

The above ingredients per tablet are compressed in the conventional manner to provide tablets. Where necessary, the tablets can be sugar-coated.

Formulation Example 2

Ophthalmic Solution

| | |
|---|---|
| 4-[(4-Diphenylmethyl-1-piperazinyl)methyl]phenyl-acetic acid | 100 mg |
| Boric acid | 700 mg |
| Borax | 400 mg |
| Sodium chloride | 500 mg |
| Methyl p-hydroxybenzoate | 26 mg |
| Propyl p-hydroxybenzoate | 14 mg |
| Sterilized pure water | to make 100 ml |

The above ingredients are mixed in the conventional manner to provide an ophthalmic solution.

Formulation Example 3

Ointment

4-[(4-Diphenylmethyl-1-piperazinyl)methyl]phenylacetic acid 500 mg Hydrophilic ointment base to make 100 ml The above ingredients are mixed in the conventional manner to provide an ointment.

Formulation Example 4

Ophthalmic Solution

| | |
|---|---|
| 4-[[4-(2-Methoxyphenyl)-1-piperazinyl]methyl]phenylacetic acid | 500 mg |
| Boric acid | 800 mg |
| Borax | 200 mg |
| Sodium chloride | 500 mg |
| Chlorobutanol | 300 mg |
| Sterilized pure water | to make 100 ml |

The above ingredients are mixed in the conventional manner to provide an ophthalmic solution.

The benzylpiperazine derivative and salt of the present invention have excellent antiallergic and antiinflammatory activities and can, therefore, be used with advantage in the treatment of various allergic diseases and inflammatory diseases.

What is claimed is:

1. A benzylpiperazine compound of formula (I) or a pharmacologically acceptable salt thereof

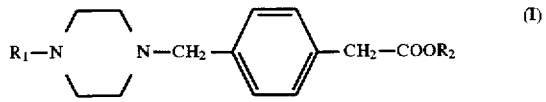

wherein $R_1$ represents a pyridine ring or a group of either formula (IV) or formula (V); $R_2$ represents hydrogen or lower alkyl

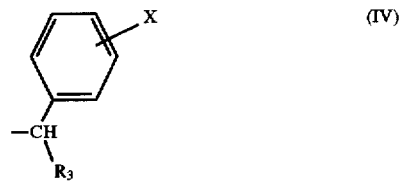

wherein $R_3$ represents hydrogen, lower alkyl, a pyridine ring or a benzene ring which may be substituted by halogen; X represents halogen

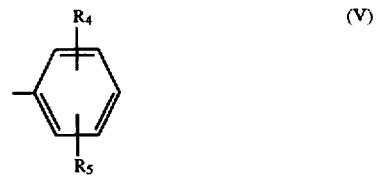

wherein $R_4$ and $R_5$ may be the same or different and each represents hydrogen, lower alkyl, lower alkoxy, halogen or carboxy.

2. The benzylpiperazine derivative or pharmacologically acceptable salt of claim 1, which is methyl 4-[(4-diphenylmethyl-1-piperazinyl)methyl]phenylacetate.

3. The benzylpiperazine derivative or pharmacologically acceptable salt of claim 1, which is 4-[(4-diphenylmethyl-1-piperazinyl)methyl]phenylacetic acid.

4. The benzylpiperazine derivative or pharmacologically acceptable salt of claim 1, which is 4-[[4-(2-methoxyphenyl)-1-piperazinyl]methyl]phenylacetic acid.

5. The benzylpiperazine derivative or pharmacologically acceptable salt of claim 1, which is 4-[[4-(2-carboxyphenyl)-1-piperazinyl]methyl]phenylacetic acid.

6. The benzylpiperazine derivative or pharmacologically acceptable salt of claim 1, which is 4-[[4-(2-pyridyl)-1-piperazinyl]methyl]phenylacetic acid.

7. The benzylpiperazine derivative or pharmacologically acceptable salt of claim 1, which is 4-[[4-(2-tolyl)-1-piperazinyl]methyl]phenylacetic acid.

8. The benzylpiperazine derivative or pharmacologically acceptable salt of claim 1, which is 4-[(4-phenyl-1-piperazinyl)methyl]phenylacetic acid.

9. The benzylpiperazine derivative or pharmacologically acceptable salt of claim 1, which is 4-[[4-(2-fluorophenyl)-1-piperazinyl]methyl]phenylacetic acid.

10. The benzylpiperazine derivative or pharmacologically acceptable salt of claim 1, which is 4-[[4-(2,5-dimethylphenyl)-1-piperazinyl]methyl]phenylacetic acid.

11. The benzylpiperazine derivative or pharmacologically acceptable salt of claim 1, which is 4-[[4-(4-methoxyphenyl)-1-piperazinyl]methyl]phenylacetic acid.

12. The benzylpiperazine derivative or pharmacologically acceptable salt of claim 1, which is 4-[[4-(3-methoxyphenyl)-1-piperazinyl]methyl]phenylacetic acid.

13. The benzylpiperazine derivative or pharmacologically acceptable salt of claim 1, which is 4-||4-(3-trifluoromethylpheneyl)-1-piperazinyl|methyl|phenylacetic acid.

14. The benzylpiperazine derivative or pharmacologically acceptable salt of claim 1, which is methyl 4-||4-|phenyl-(2-pyridyl)methyl|-1-piperazinyl|methyl|phenylacetate.

15. The benzylpiperazine derivative or pharmacologically acceptable salt of claim 1, which is 4-||4-|phenyl-(2-piridyl)methyl|-1-piperazinyl|methyl|phenylacetic acid.

16. The benzylpiperazine derivative or pharmacologically acceptable salt of claim 1, which is methyl 4-||4-|(4-chlorophenyl)phenylmethyl|-1-piperazinyl|methyl| phenylacetate.

17. The benzylpiperazine derivative or pharmacologically acceptable salt of claim 1, which is 4-||4-|(4-chlorophenyl)phenylmethyl|-1-piperazinyl|methyl|phenylacetic acid.

18. A process for synthesizing the benzylpiperazine derivative or pharmacologically acceptable salt claimed in claim 1, which comprises reacting a piperazine derivative of the following formula (II) with a 4-halomethylphenylacetic acid ester of the following formula (III), followed where necessary by hydrolyzing of the reaction product

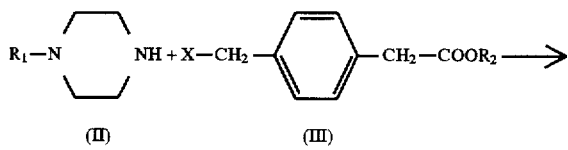

(II)  (III)

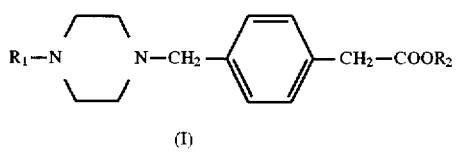

(I)

19. An anti-allergic composition which comprises an antiallergic effective amount of a benzylpiperazine compound or a pharmacologically acceptable salt thereof as defined in claim 1 and a pharmacologically acceptable carrier therefor.

20. An anti-inflammatory composition which comprises an anti-inflammatory effective amount of a benzylpiperazine compound or a pharmacologically acceptable salt thereof as defined in claim 1 and a pharmacologically acceptable carrier therefor.

21. A method of treating allergic disease which comprises administering to a patient in need thereof an effective amount of a benzylpiperazine compound or a pharmacologically acceptable salt thereof as claimed in claim 1.

22. A method of treating inflammatory disease which comprises administering to a patient in need thereof an effective amount of a benzylpiperazine compound of pharmacologically acceptable salt thereof as claimed in claim 1.

* * * * *